(12) United States Patent
Bramlet et al.

(10) Patent No.: US 6,648,889 B2
(45) Date of Patent: Nov. 18, 2003

(54) INTRAMEDULLARY HIP NAIL WITH BIFURCATED LOCK

(76) Inventors: Dale G. Bramlet, 2044 Brightwaters Blvd., NE., St. Petersburg, FL (US) 33704; Patrick J. Cosgrove, 12200 4th St. E., Treasure Island, FL (US) 33706; John A. Sodeika, 11650 Harborside Cir., Largo, FL (US) 33773; Peter M. Sterghos, 5291 40th Ave., St. Petersburg, FL (US) 33709

( * ) Notice: Subject to any disclaimer, the term of this patent is extended or adjusted under 35 U.S.C. 154(b) by 64 days.

(21) Appl. No.: 09/982,152

(22) Filed: Oct. 17, 2001

(65) Prior Publication Data

US 2002/0156473 A1 Oct. 24, 2002

Related U.S. Application Data

(63) Continuation-in-part of application No. 09/841,851, filed on Apr. 24, 2001.

(51) Int. Cl.[7] ............................................. A61B 17/56
(52) U.S. Cl. ........................... 606/62; 606/65; 606/72
(58) Field of Search .............................. 606/62, 64, 65, 606/60, 63, 66, 67, 68, 70, 72, 73, 81, 89

(56) References Cited

U.S. PATENT DOCUMENTS

| | | | |
|---|---|---|---|
| 4,227,518 A | 10/1980 | Aginsky | |
| 4,236,512 A | 12/1980 | Aginsky | |
| 4,275,717 A | 6/1981 | Bolesky | |
| 4,453,539 A | 6/1984 | Raftopoulos et al. | |
| 4,519,100 A | 5/1985 | Wills et al. | |
| 4,590,930 A | 5/1986 | Kurth et al. | |
| 4,632,101 A | 12/1986 | Freedland | |
| 4,721,103 A | 1/1988 | Freedland | |
| 4,862,883 A | 9/1989 | Freeland | |
| 5,032,125 A | * 7/1991 | Durham et al. | 606/62 |
| 5,041,114 A | 8/1991 | Chapman et al. | |
| 5,057,103 A | 10/1991 | Davis | |
| 5,176,681 A | 1/1993 | Lawes et al. | |
| 5,454,813 A | * 10/1995 | Lawes | 606/62 |
| 5,810,820 A | 9/1998 | Santori et al. | |
| 5,928,235 A | * 7/1999 | Friedl | 606/64 |
| 5,971,986 A | 10/1999 | Santori et al. | |
| 5,976,139 A | 11/1999 | Bramlet | |
| 6,077,264 A | * 6/2000 | Chemello | 606/67 |
| 6,126,661 A | 10/2000 | Faccioli et al. | |
| 6,183,474 B1 | * 2/2001 | Bramlet et al. | 606/66 |
| 6,235,031 B1 | * 5/2001 | Hodgeman et al. | 606/64 |
| 6,443,954 B1 | * 9/2002 | Bramlet et al. | 606/62 |

FOREIGN PATENT DOCUMENTS

| | | |
|---|---|---|
| DE | 2 260 839 | 6/1974 |
| DE | 24 04 441 | 7/1975 |
| DE | 34 13 690 | 10/1985 |
| EP | 0 441 577 | 8/1991 |
| EP | 0 922 437 | 6/1999 |
| WO | WO 00/76414 | 12/2000 |
| WO | WO 02/067794 | 9/2002 |

* cited by examiner

*Primary Examiner*—Pedro Philogene
(74) *Attorney, Agent, or Firm*—McHale & Slavin, P.A.

(57) ABSTRACT

The intramedullary nail system includes an intramedullary nail for insertion in the femur. The nail has an axial bore and an intersecting transverse bore. A lag screw is inserted through the transverse bore and turned into the head of the femur. A slotted sleeve is inserted over the lag screw and through the transverse bore with the slots aligned with the axial bore. A sleeve lock is inserted into the axial bore and has a locking tab which engages the slots in the sleeve preventing rotational and longitudinal movement between the sleeve and the nail. A compression screw is turned into the trailing end of the lag screw and engages the encircling sleeve to provide longitudinal translation between the lag screw and sleeve to apply compressive force across a fracture.

16 Claims, 10 Drawing Sheets

NAIL NOT SHOWN
FOR CLARITY

NAIL NOT SHOWN
FOR CLARITY

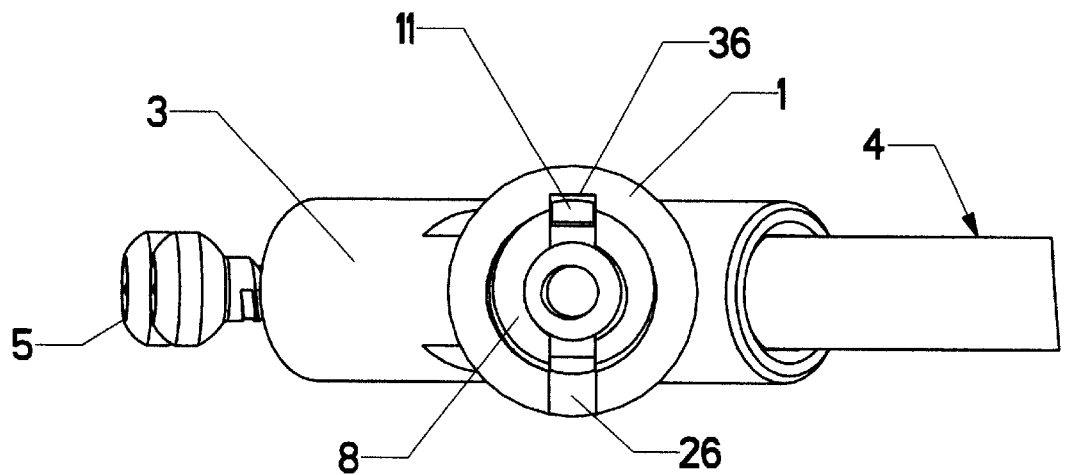
FIG. 6
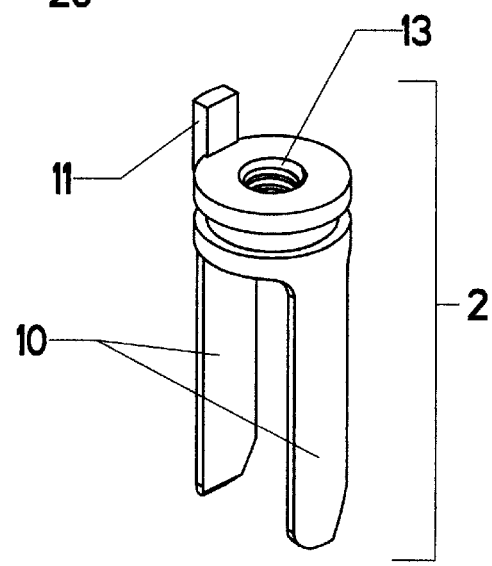
FIG. 7
FIG. 8
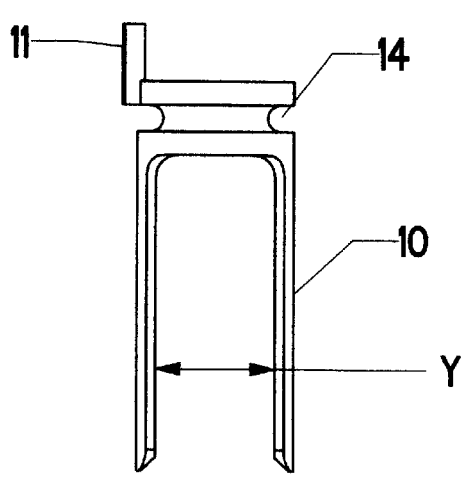
FIG. 9
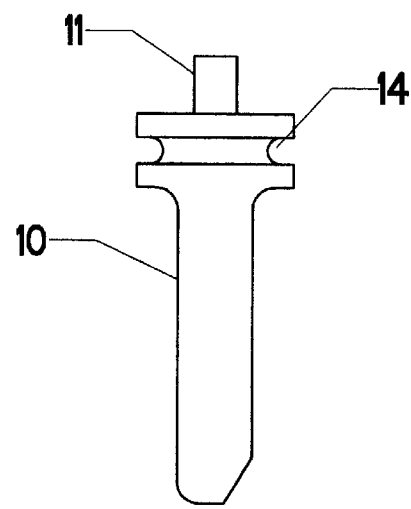
FIG. 10

NAIL NOT SHOWN
FOR CLARITY

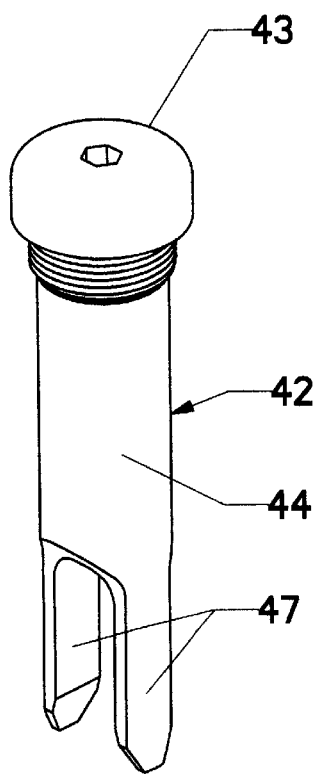
FIG. 33
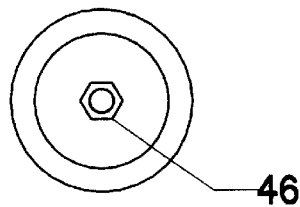
FIG. 34
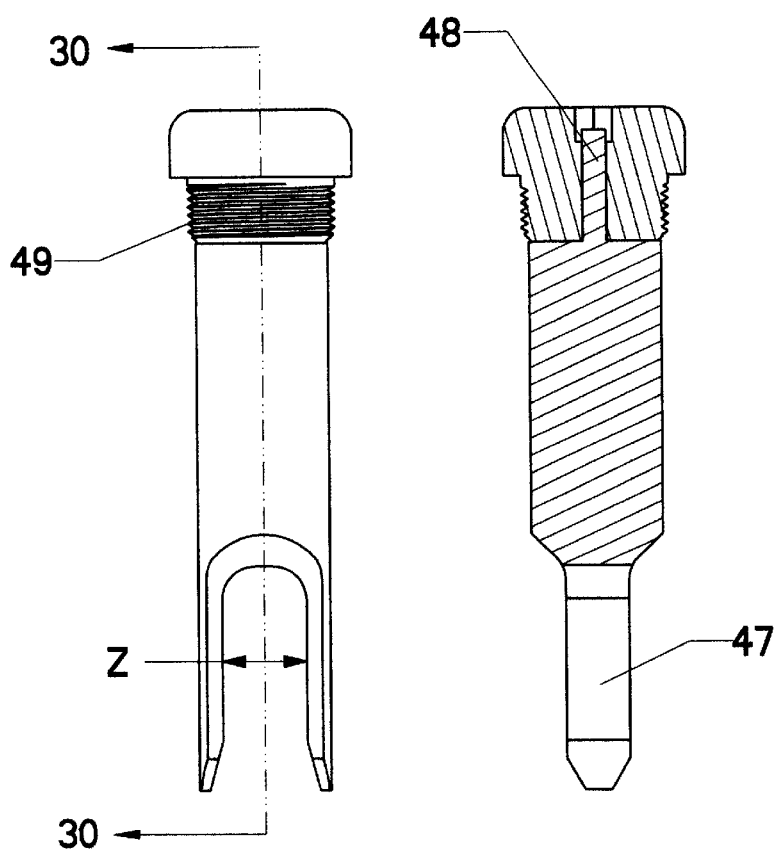
FIG. 35
FIG. 36

INTRAMEDULLARY HIP NAIL WITH BIFURCATED LOCK

This application is a continuation-in-part of U.S. application Ser. No. 09/841,851, filed Apr. 24, 2001.

FIELD OF THE INVENTION

The present invention generally relates to an intramedullary system for coupling first and second bone portions across a fracture therebetween and, more specifically, to an intramedullary hip pinning system for rigidly interconnecting a femoral head to the remaining portion of the femur and across a fracture in the area of the femoral neck.

BACKGROUND OF THE INVENTION

The intramedullary nail was introduced in the 1930's. This device was inserted into the intramedullary canal of the femur resulting in immediate fixation of fractures, early mobilization of the patient, and a lower morbidity and mortality. A number of nails have been introduced for fracture fixation about the femur in proximal end, including the Jewett Nail and Enders Nail.

Intramedullary nails were also inserted down the entire length of the femoral canal to provide a basis for the construct. Threaded wires, standard bone screws or cannulated bone screws were then inserted through or along side the proximal nail and into the femoral head to provide fixation and rotational stability. Compression of the proximal bone fragments against each other was not available and in longer nails the distal tip of the nail tends to rotate out of plane which forces the surgeon to locate the distal screw holes using fluoroscopy by a method commonly known as "free-handing".

In the 1960s, the compression hip screw was introduced, resulting in improved fixation of the proximal femur. A lag screw assembly was inserted into the femoral head, a plate was attached to the lateral femur, and a compression screw joined the two. These implants provided a more rigid structure for the patient and allowed the surgeon to compress the fractured fragments against each other thereby decreasing the time to mobility. A number of compression hip screws have been introduced for fracture fixation about the proximal femur.

During implantation typical compression hip screws require an incision at least equal to the length of plate being used which extends operative time and blood loss. The side plate also creates a protuberance on the lateral side which provides an annoyance to the patient. Compression hip screw systems also fail to provide adequate compression in oseteogenic patients because the lag screw threads fail to obtain sufficient purchase due to poor bone stock. Poor purchase is known to contribute to nonunion, malunion and the lag screw assembly eroding through the superior bone of the head of the femur in a condition known as "cut out". Additionally, many patients are dissatisfied with the results of compression hip screw surgery because of the excessive sliding to a medial displacement and shortening position which leads to a change in gait.

Newer devices and inventions explored additions to the nail and lag screw assembly to improve the fixation and ease or eliminate the need to locate the distal screw holes. These newer devices are commonly classified as "expanding devices" and expand in size, after placement, to fill the intramedullary cavity. Freedland, U.S. Pat. Nos. 4,632,101, 4,862,883 and 4,721,103, Chemello, U.S. Pat. No. 6,077,264 and Davis, U.S. Pat. No. 5,057,103 describe a method of fixation which provides points which contact the internal cortical wall. In these patents a mechanism is actuated deploying arms or anchor blades through the cancellous bone to contact the inner cortical wall. These methods are complex, do not deploy through the cortical bone and are difficult to retract should the nail or lag screw assembly require extraction.

Other expanding devices provide surface contact with the internal cortical wall resulting in a wedge effect. Kurth, U.S. Pat. No. 4,590,930, Raftopoulos, U.S. Pat. No. 4,453,539 and Aginski, U.S. Pat. No. 4,236,512 among others have described mechanisms which deploy or expand with a molly bolt concept. These methods are complex and difficult to retract should the nail or lag screw assembly requires extraction and do not deploy through the cortical bone.

Bolesky, U.S. Pat. No. 4,275,717, was the first to discuss engagement within the cortical wall. However, Bolesky's invention does not address controlled penetration into the wall and required permanent implantation of the actuation rod. In addition, Bolesky does not address the fundamental problem of the actuation rod's protrusion extramedullarly into the surrounding musculature.

In earlier patents, U.S. Pat. Nos. 5,976,139 and 6,183,474 B1, both incorporated herein by reference, Bramlet describes a surgical anchor which has deployable tangs. These tangs are simple design, internally positioned, yet easily deployed into, and if desired through, the cortical bone providing improved purchase for compression of a fracture; especially in osteogenic bone. These tangs are just as easily retracted should the device require explantation.

In 1988 Lawes, et. al., U.S. Pat. No. 5,176,681, disclosed a method of combining desirable aspects of both intramedullary nails and compression hip screws. Lawes described a method for joining the lag screw and nail to resist loosening or moving of the lag screw during the operation. Approximately 10 years ago Howmedica (Rutherford, N.J., United States) was the first to produce the "Gamma Nail", named for its similarity in shape to the Greek letter, as an intramedullary hip compression screw device and other designs soon followed.

In 1990 Durham, et. al., U.S. Pat. No. 5,032,125, disclosed an intramedullary hip compression screw system which incorporated a sleeve for slidably receiving the lag screw. A set screw was then used to engage the sleeve thereby preventing translation and rotation of the sleeve. This device allowed for reduction of the proximal fragment using the same method as conventional hip screw assemblies. Shortly thereafter Smith & Nephew Richards (Memphis, Tenn., United States) produced the "Intramedullary Hip Compression Screw".

These intramedullary hip compression screw systems required a few small incisions, allowed capture of the most proximal fragments of the femur, rigid fixation of the most proximal and distal fragments, and a sliding lag screw assembly which allows reduction of the fragments as the patient ambulates or begins to bear weight on the fractured limb. These nails are typically held in place on the distal end through interference forces with the intramedullary canal and through the use of locking screws.

The typical intramedullary hip compression screw's shape accommodates the relative shape of the greater trochanter and femoral shaft, neck and head fragments. Therefore, the shape of the hip is preserved. Indications for use of a compression hip screw are expanded because fractures to the subtrochanteric region of the proximal femur, as well as reverse obliquity fractures can be treated more efficiently. Additionally, the bulk of an intramedullary hip screw blocks excessive sliding of the proximal fragment.

Current intramedullary compression hip screw systems continue to suffer from some of the same problems exhibited in those of its predecessors. Osteogenic bone still provides a poor medium for purchase of the lag screw assembly thread inhibiting adequate compression and rotational stability. Longer nails continue to see the distal tip of the nail rotating out of plane forcing the surgeon to locate the distal screw holes by the free-hand method. The free-handing technique leads to an increased surgical time and exposes the surgeon and patient to increased radiation dosages.

Current intramedullary compression hip screw systems also provide new limitations that hamper their effectiveness. One such limitation is evident in both Lawes' and Durham's designs. These designs require the use of a set screw to prevent rotation of the lag screw; the set screw in the Lawes patent interacts directly with the lag screw, while Durham's is indirect with the lag screw. To ensure proper mating takes place the Smith & Nephew Richards' systems provides a torque wrench, while Howmedica's system requires tightening of the set screw to full engagement and then backing it off. Over time, loss of calibration of the torque wrench and improper engagement by the surgeon user could lead to an unsatisfactory engagement and decreased usefulness.

Clearly a need exists for a system that is superior to the conventional compression hip screws while minimizing the surgical insult to the human body.

SUMMARY OF THE INVENTION

Therefore, it is an object of this invention to teach a simple, effective and controllable fixation device which allows greater purchase of the lag screw assembly within the femoral head resulting in improved compression across the fracture line.

It is another object of this invention to teach a system with rotational stability both in the femoral head and in the femoral shaft, and that offers to minimize, if not eliminate the need for additional distal incisions to locate and place locking screws.

It is yet another objective of this invention to teach an intramedullary hip nail system that provides for a more positive, and more repeatable engagement mechanism for allowing the lag screw to slide during fracture reduction and healing.

It is a further objective of this invention to teach a system designed to allow the surgeon a choice of penetration distance within the femoral head and femoral shaft fixation based upon the injuries presented and the desired level of treatment.

It is a still further objective of this invention to teach a system that allows explantation to occur as easily as implantation.

An intramedullary nail system for coupling first and second bone portions across a fracture therebetween may be provided as a kit of several assembled subassemblies. The subassemblies of the intramedullary nail system according to the invention are combined for installation within the medullary canal of a fractured bone, such as a femur.

In one embodiment of the present invention, the intramedullary nail system includes an intramedullary nail body having an internally threaded trailing end and a leading end with portals which allow passage of cortical screws. The nail body has a transverse bore near the trailing end in communication with the cannulated axial bore for recieving a lag screw assembly. The lag screw assembly has a leading end with an externally threaded portion with portals which allow passage of anchoring tangs and internally deployable and retractable anchoring tangs. The lag screw assembly has internal threads on the trailing end. A slotted sleeve slidably passes through the transverse clearance bore of intramedullary nail and freely telescopes over the lag screw assembly while preventing rotation of lag screw assembly, but allowing axial translation of the lag screw. A compression screw has a shoulder contacting the trailing end of the slotted sleeve and engages the internal threads of the lag screw assembly trailing end providing axial translation of the lag screw assembly within the sleeve. A sleeve lock passes through the axial bore of the intramedullary nail and along the slotted sleeve through its slot(s) thereby preventing rotation and axial translation of the sleeve, but allowing axial translation of the lag screw assembly. An end cap assembly with external threads engages the internal threads of the trailing end of the intramedullary nail.

A preferred embodiment combines the intramedullary nail, the sleeve lock and the end cap assembly into an intramedullary nail assembly. When presented as such, the surgeon or surgical assistant will not have to enjoin these items during the surgical procedure.

The end cap assembly preferably contains a patch of ultra-high molecular weight poly-ethylene (UHMWPE) within the threads. This provides constant positive engagement between the end cap external threads and the intramedullary nail internal threads.

With the intramedullary nail placed into position within the intramedullary canal the lag screw assembly is then placed into position in a manner consistent with common technique. The unique tang assembly is actuated and the tangs are deployed to any desired position thereby achieving the desired level of fixation based upon the quality of the bone.

The lag screw assembly preferably contains a permanently placed anchoring tang assembly stored in a retracted position within the leading end. The tangs are deployed or retracted from the trailing end of the lag screw assembly.

The slotted sleeve is coaxially inserted over the lag screw assembly's trailing end and through the intramedullary nail. The slotted sleeve is aligned to accept the sleeve lock.

The sleeve lock is actuated via a mechanism in the intramedullary nail insertion instrument. The sleeve lock moves from its primary position to its final position. In its final position the sleeve lock passes through the slotted sleeve slots preventing rotation and axial translation of the slotted sleeve.

The compression screw passes through the sleeve and engages the lag screw assembly. As the compression screw is tightened the lag screw assembly and associated first bone portion are pulled against the intramedullary nail and second bone portion resulting in compressive forces being applied across the fracture.

The compression screw preferably contains a patch of ultra-high molecular weight poly-ethylene (UHMWPE) within the threads. This provides constant positive engagement between the compression screw external threads and the lag screw assembly internal threads.

The cortical screws are then placed into position through the bone and through the intramedullary nail in a manner consistent with common technique.

In another embodiment of the present invention the intramedullary nail system includes a intramedullary nail with portals at the leading end which allow passage of cortical screws and/or anchoring tangs. When the intramedullary nail is placed into position the anchoring tang assembly is actuated to deploy the tangs out from their stowed position into the cortical bone. The tangs are deployed to any desired position thereby achieving a desired fixation and rotation prevention based upon the quality of the bone. Should the system require additional load carrying capability, cortical screws may be placed to enjoin the intramedullary nail with the surrounding cortical bone.

The intramedullary nail of this alternate embodiment is preferably cannulated to allow passage of one or more anchoring tang assemblies. These anchoring tang assemblies are inserted from the trailing end towards the leading end and the tangs deployed by means of an actuator driver. An alternate embodiment of the intramedullary nail has a retracted anchoring tang assembly, which is permanently placed within the leading end of the intramedullary nail and is deployed or retracted by means of an actuator driver from the trailing end of the intramedullary nail.

The anchoring tang assembly contains arcurate shaped tangs that are permanently attached to the assembly's main body. These tangs are initially formed into a prescribed position for storage. As the assembly is actuated, and the tangs deploy, the tangs are formed into their final shape through interaction with the portal of either the intramedullary nail or the lag screw assembly.

The lag screw assembly preferably contains a permanently placed anchoring tang assembly stored in a retracted position within the leading end. The tangs are deployed or retracted from the trailing end of the lag screw assembly.

The anchoring tang assembly within the lag screw is similar in design to that within the intramedullary nail in that it contains arcurate shaped tangs that are permanently attached to the assembly's tang body. These tangs are initially formed into a prescribed position for storage. As the assembly is actuated, and the tangs deploy, the tangs are formed into their final shape through interaction with the portal of either the intramedullary nail or the lag screw assembly.

The end cap preferably contains a patch of ultra-high molecular weight poly-ethylene (UHMWPE) within the threads. This provides constant positive engagement between the end cap external threads and the intramedullary nail internal threads. In its final position the end cap locks the sleeve and inhibits the sleeve from sliding or rotating out of a prescribed position.

The intramedullary nail system may be supplied as a kit with subassemblies to be combined into the complete system during the surgical procedure.

DESCRIPTION OF THE DRAWINGS

FIG. 6, is a top view of the Intramedullary Nail System of FIG. 2;

FIG. 7, is a top view of FIG. 8;

FIG. 8, is an isometric view of the Sleeve Lock;

FIG. 9, is a front view of FIG. 8;

FIG. 10, is a side view of FIG. 8;

FIG. 33, is an isometric view of the alternate embodiment Sleeve Lock;

FIG. 34, is a top view of FIG. 33;

FIG. 35, is a front view of FIG. 33; and

FIG. 36, is a cross section view of FIG. 33

DETAILED DESCRIPTION

Figure 1:
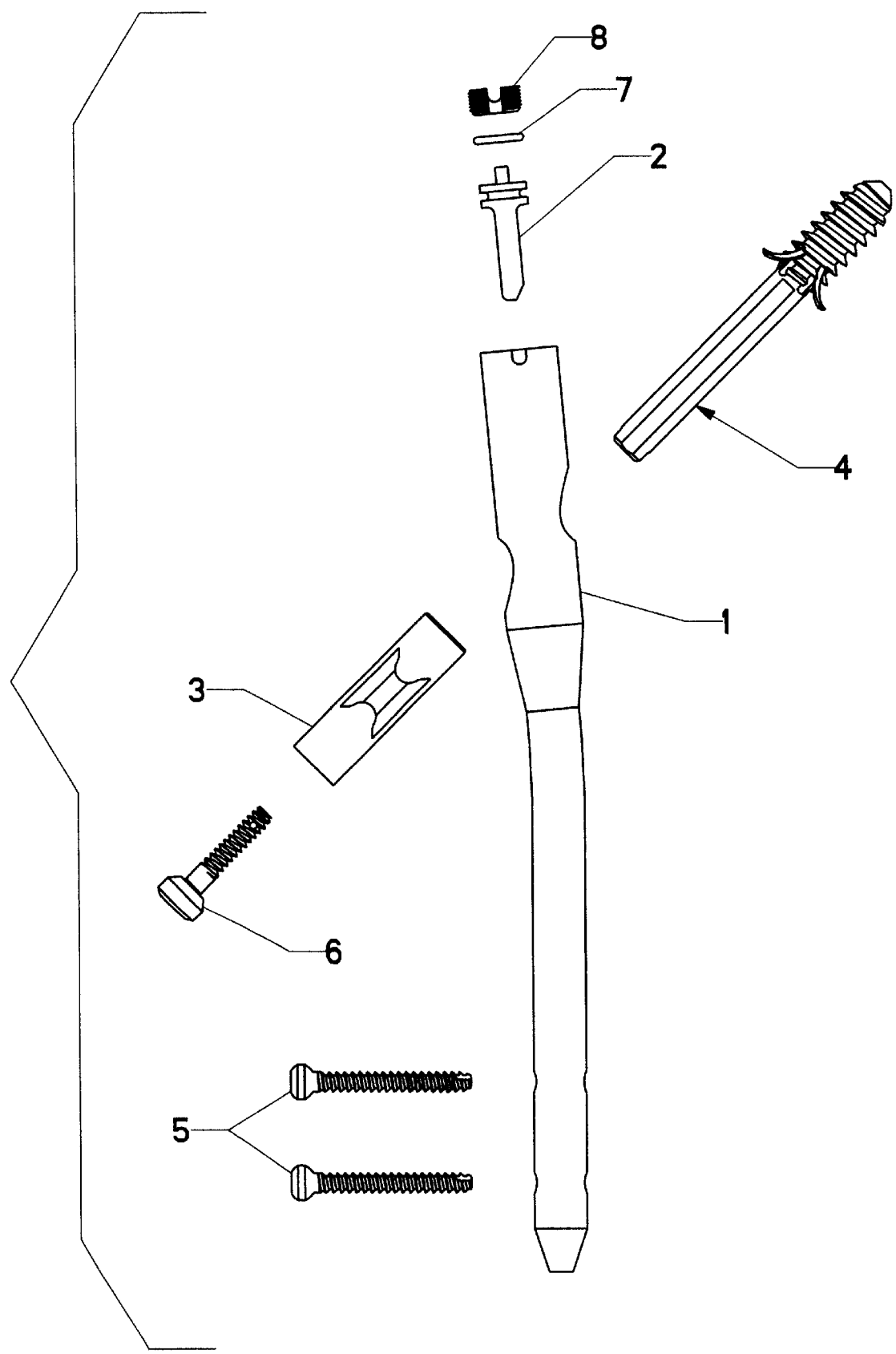
FIG. 1, is a longitudinal view of the preferred embodiment Intramedullary Nail System in an exploded state.

The individual components of the assembly, as illustrated in FIG. 1, are constructed of implantable grade stainless steel alloys in the preferred embodiment but could also be constructed of implantable grade titanium alloys or polymeric materials such as nylon, carbon fibers and thermoplastics, as well. These components consist of the lag screw assembly 4, the nail body 1, the sleeve 3, the compression screw 6, the end cap 8, snap ring 7, sleeve lock 2 and the cortical screws 5 (FIG. 1).

Figures 2, 3:
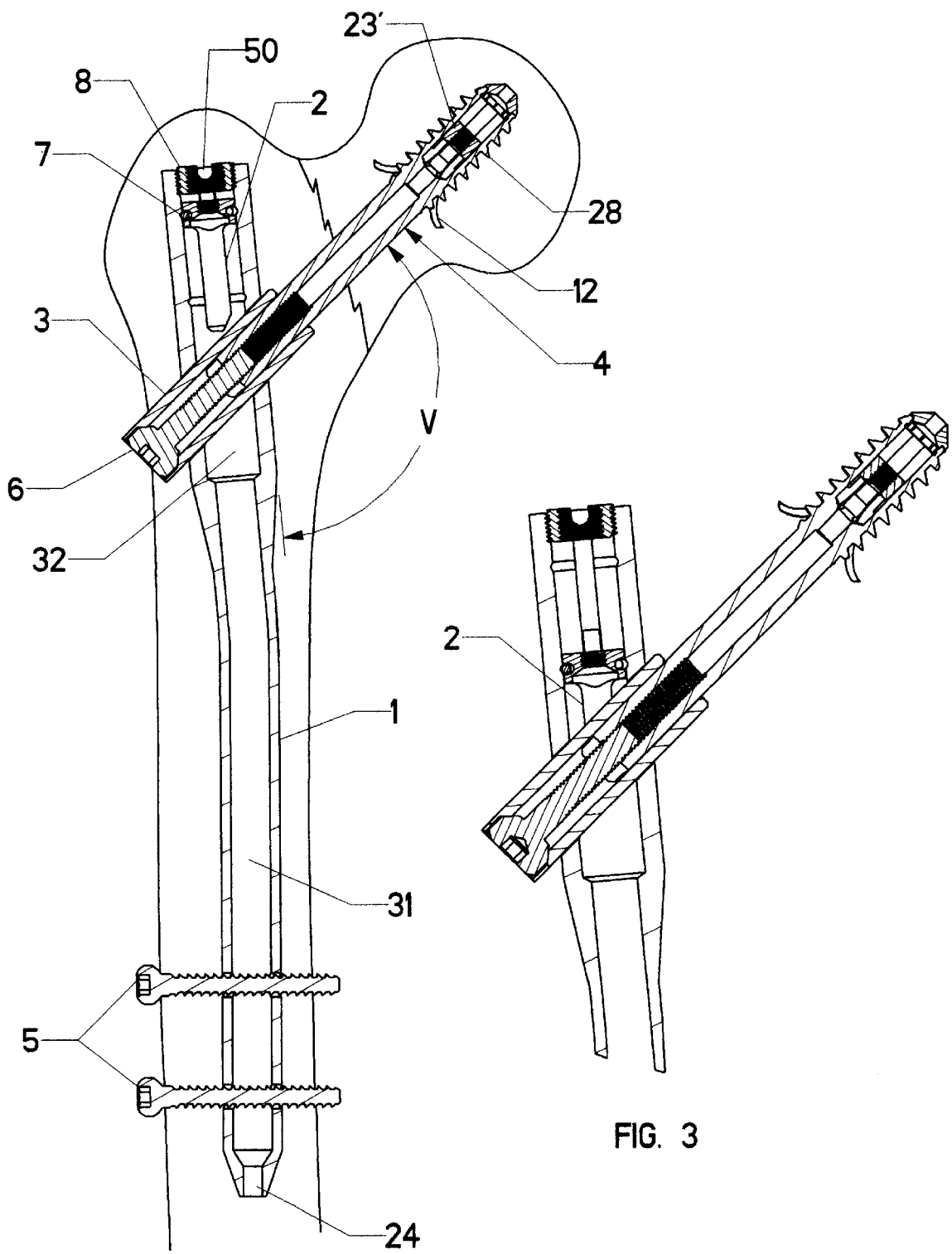
FIG. 2, is a view, partially in longitudinal cross section, of the Intramedullary Nail System placed in the intramedullary canal of a fractured bone using cortical screws as a method of fixation.
FIG. 3, is an enlarged, cross section view of the proximal portion of the Intramedullary Nail System in FIG. 2.
Figure 4:
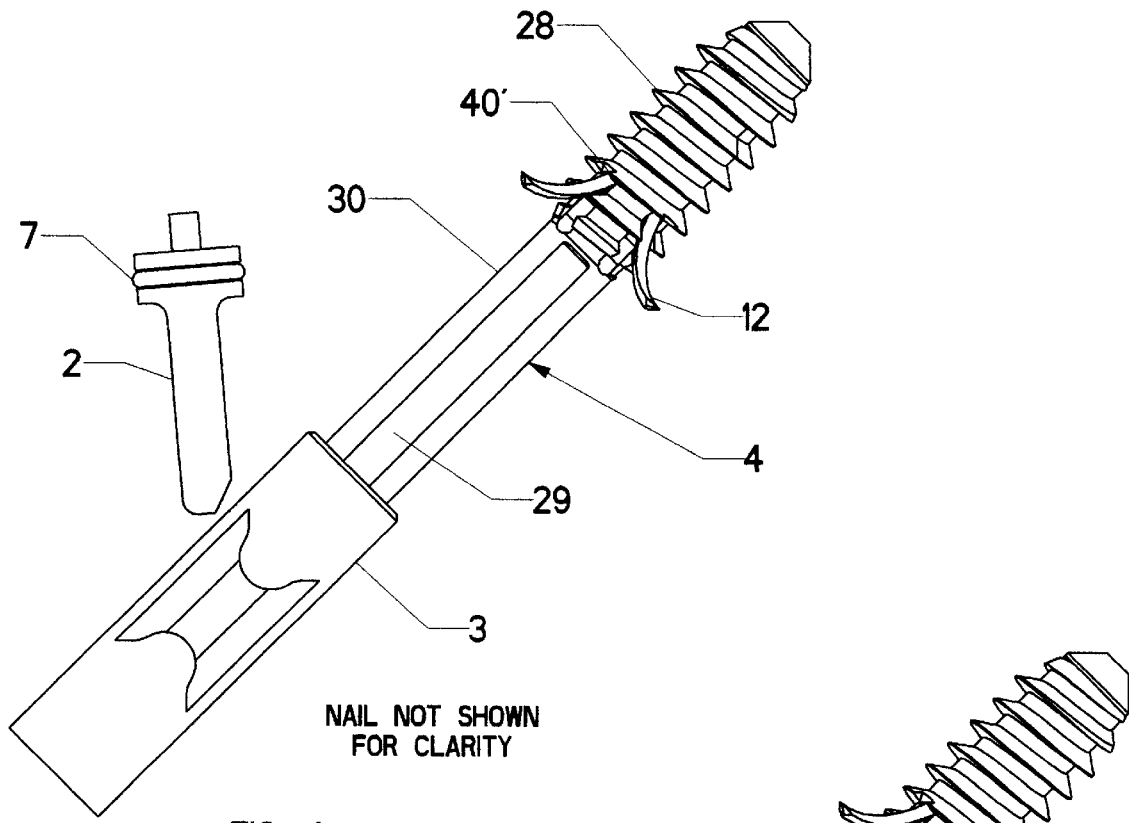
FIG. 4, is an enlarged view of the proximal portion of the Intramedullary Nail System of FIG. 2.

The lag screw assembly 4 is described in detail in U.S. Pat. No. 6,183,474 B1, as is compression screw 6. The external features of the lag screw assembly 4 are indicated in FIG. 4 and include the threads 28, the tang 12, the body 30 and the flats 29 on the body 30. The threads 28 engage the cancellous bone within the femoral head on the proximal side of the fracture line; the tang body 23' carries the tang 12 which is also located on the proximal side of the fracture line and engages cortical bone as shown in FIG. 2 deployed in the femur. However, the tang 12 is fully retracted into the body of the lag screw in its as-delivered state and remains that way until the lag screw assembly is fully positioned within the femoral head. When deployed in the femoral head, the tang 12 extends through exit hole 40' and penetrates the cortical bone, greatly increasing purchase axial fixation and rotational stability of the lag screw assembly. The tang is fully reversible if removal of the lag screw is ever required. The body 30 of lag screw assembly 4 has with two flats 29 180 degrees apart (FIG. 4) which interfaces with bore 38 and end configuration flats 17 (FIGS. 11,12,13) of the sleeve 3 in such a way as to allow axial translation or slide of the lag screw while preventing rotation relative to the sleeve 3. This sliding prevents penetration of the femoral head by the proximal end of the lag screw as the fracture compresses from patient load bearing.

Figure 20:
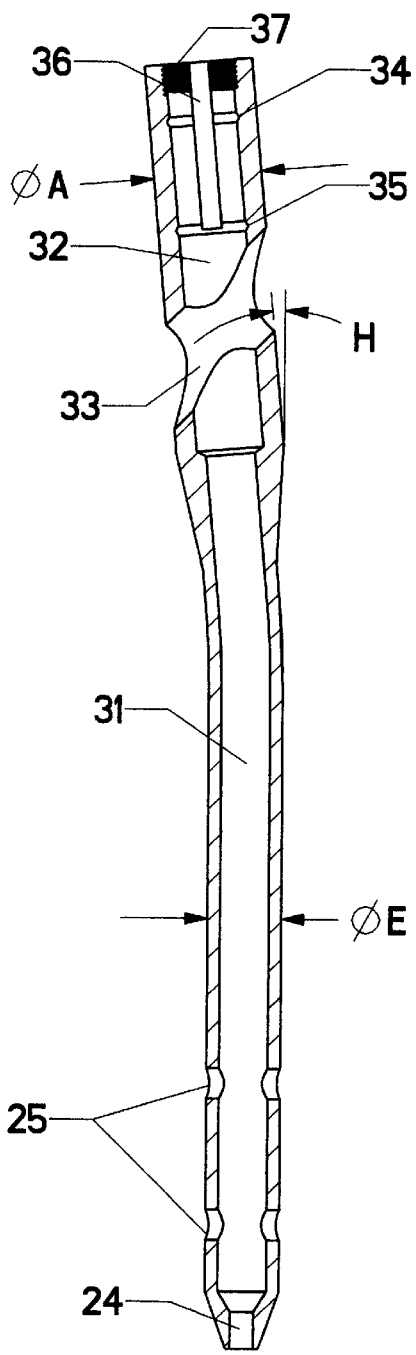
FIG. 20, is a section view of FIG. 21.
Figure 21:
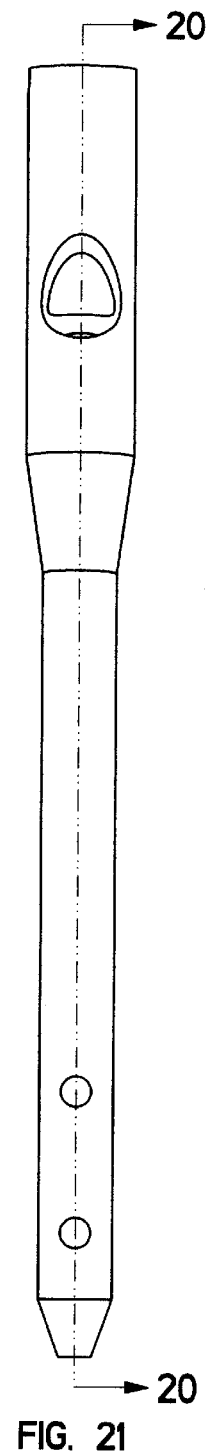
FIG. 21, is a front view of the Intramedullary Nail.

The nail body 1 is designed for antegrade insertion into the intramedullary canal of the femur. It is anatomically shaped to the axis of the canal and has a mediolateral bend angle H (FIG. 20). The proximal outside diameter A of the body is greater than the distal outside diameter E due to narrowing of the canal and to allow the lag screw cylindrical clearance bore 33 (FIG. 20) to be large enough to pass the thread 28 of the lag screw assembly 4 and provide a sliding fit to the outside diameter of the sleeve 3. The axis of clearance bore 33 is at an angle V with respect to the proximal diametral axis (FIG. 2). This angle V allows proper positioning of lag screw assembly 4 within the femoral head. The nail proximal bore 32, distal bore 31 and distal end bore 24 are of circular cross section. Bores 32, 31 and distal end bore 24 are sized to permit a clearance and sliding fit, respectively, with a guide pin (not illustrated) during installation of the nail body 1 into the intramedullary canal.

The clearance holes 25 of nail body 1 pass through the distal outside surface and wall of the nail body 1, into the distal bore 31 and continue on the same axis through the opposite wall and outer diameter. Their diameter is such as to allow passage of the threaded portion of the cortical screw 5. (FIG. 2). The nail body 1 is secured both in axial translation and rotation within the intramedullary canal by cortical screws 5 when they are installed through the lateral cortex, clearance holes 25, and the medial cortex of the femur as illustrated in FIG. 2.

Figure 19:
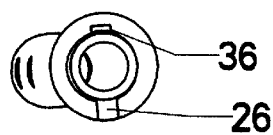
FIG. 19, is a top view of FIG. 21.
Figure 22:
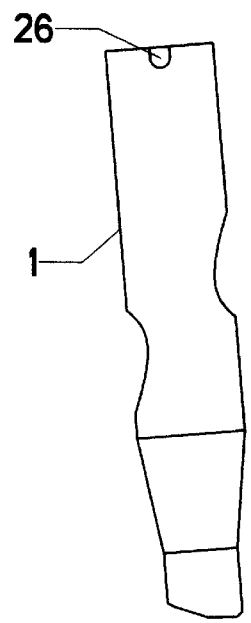
FIG. 22, is an enlarged, partial side view of FIG. 21.

The internal threads 37 (FIG. 20) at the proximal end of the nail body 1 provide for instrument interface and end cap 8 retention. The threads 37 are used for attachment of a nail removal instrument (not shown). The internal threads 37 also engage the external threads 15 (FIG. 16) of end cap 8. A slot 26 (FIGS. 19, 22) extends through the proximal nail body wall and internal threads 37 breaking into the nail proximal bore 32. Slot 26 is utilized for instrument interface and instrument and end cap 8 anti-rotation. The sleeve lock anti-rotation groove 36 (FIGS. 19, 20) is located in the nail proximal bore 32 and 180 degrees around the nail body proximal diameter from slot 26. Groove 36 extends from the surface of the nail proximal internal bore 32 into the nail proximal wall a given constant depth but not through the wall. It extends axially a given distance, through threads 37 and exits the proximal end of nail body 1 (FIGS. 19, 20). Also located in the nail body 1 proximal bore 32, are proximal circumferential groove 34 and distal circumferential groove 35 (FIG. 20).

The sleeve lock 2 (FIG. 1), has a basic cylindrical cross section with two integral locking tabs 10 (FIGS. 8, 9,10). Each locking tab 10 has a semi-circular cross section, with the radius being the same as that of the cylindrical body section. A circumferential groove 14 is located in the cylindrical body section and is sized to accept snap ring 7 (FIG. 1). An anti-rotation tab 11 (FIGS. 7, 8, 9, 10) is an integral part of sleeve lock 2, which protrudes radially and axially from the cylindrical body section and is sized for a sliding fit within nail body 1 anti-rotation groove 36. A threaded bore 13 (FIGS. 7,8) extends axially through the cylindrical body section. The outside diameter of sleeve lock 2 is sized for a sliding fit with proximal bore 32 of nail body 1.

Figure 23:
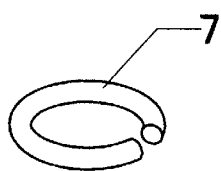
FIG. 23, is an isometric view of the Snap Ring.
Figure 24:
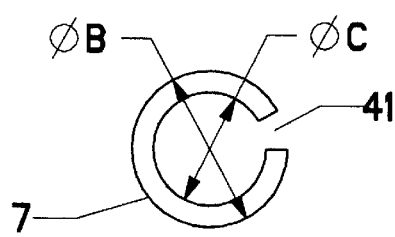
FIG. 24, is a top view of FIG. 22.

The snap ring 7 (FIG. 1), is a toroid of circular cross section with an outside diameter B and inside diameter C (FIGS. 23, 24) a gap 41 is provided in the circumference of snap ring 7 to allow radial flexure which either increases or decreases diameters B and C depending on the direction of force. The snap ring 7 is sized in such a way as to loosely fit within groove 14 of sleeve lock 2 (FIGS. 9, 10). When installed into groove 14 snap ring diameter B is larger than the outside diameter of sleeve lock 2, however, if compressed, diameter B becomes equal or less than the outside diameter of sleeve lock 2.

Figure 16:
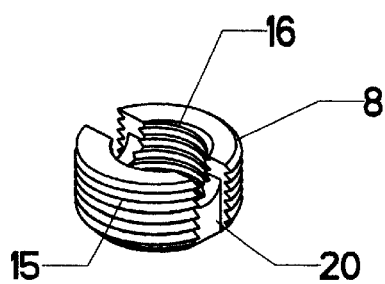
FIG. 16, is an isometric view of the End Cap Assembly.
Figure 17:
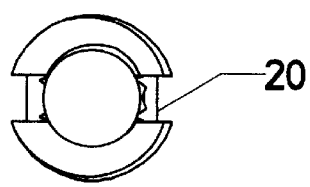
FIG. 17, is a top view of FIG. 16.
Figure 18:
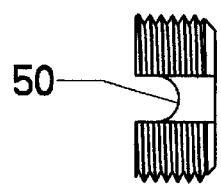
FIG. 18, is a side view of FIG. 16.

The end cap 8 (FIG. 1) is of a cylindrical cross section with a threaded outside diameter 15 and threaded internal bore 16 (FIG. 16). Two compound anti-rotation grooves run axially in the outside diameter and are located radially 180 degrees apart. The grooves consist of two sections 20 and 50 (FIGS. 16,17,18). Section 20 extends into, but not through the wall of end cap 8 whereas section 50 extends through the wall and breaks into threaded bore 16. The outside threads of end cap 8 are sized to interface with nail body 1 internal threads 37.

The nail body 1, sleeve lock 2, snap ring 7 and end cap 8 may be pre-assembled by the manufacturer and supplied to surgery as a kit assembly. The pre-assembly consists of the following steps: the snap ring 7 is expanded and placed into groove 14 of sleeve lock 2. The sleeve lock/snap ring assembly inserts into proximal bore 32 of nail body 1 with locking tabs 10 leading. Since the outside diameter B of snap ring 7 is greater than the nail body 1 proximal bore 32, snap ring 7 will stop when it contacts the proximal end of nail body 1. The sleeve lock/snap ring assembly is then rotated axially to align the sleeve lock anti-rotation tab 11 with nail body anti-rotation groove 36. The sleeve lock/snap ring assembly is inserted further into nail body 1 proximal bore 32 at which time bore 32 acts on snap ring 7 compressing it within groove 14 of sleeve lock 2 allowing the sleeve lock/snap ring assembly to slide in bore 32 and sleeve lock anti-rotation tab 11 to engage nail body 1 sleeve lock anti-rotation groove 36. As insertion continues, snap ring 7 encounters nail body 1 proximal circumferential groove 34 at which time snap ring 7 assumes its original diameter B as it expands into circumferential groove 34, locking or "detenting" the sleeve lock 2 in this position. Additional insertion force causes the snap ring 7 diameter B to interact with bore 32 compressing it back into sleeve lock 2 groove 14, allowing the sleeve lock/snap ring assembly to slide in bore 32 towards nail body 1 distal circumferential groove 35. Upon contacting circumferential groove 35, snap ring 7 will expand into groove 35 locking or "detenting" the sleeve lock 2 in this position. With the sleeve lock 2 in this position, end cap 8 can be threaded into nail body 1 internal threads 37 with groove section 20 leading. The end cap 8 is installed until its trailing end is as close to flush with the nail body 1 proximal end as practical with the end cap 8 slots 20/50 aligned radially with nail body 1 instrument interface slot 26 and nail body 1 anti-rotation slot 36. The sleeve lock 2, is now pulled from its "detented" position, with snap ring 7 located at distal circumferential groove 35 (FIG. 20), by use of an instrument (not shown) passed through end cap threaded bore 16 and threaded into sleeve lock 2 threaded bore 13. The force causes snap ring 7 to be compressed into sleeve lock 2 groove 14 which allows sleeve lock 2 to translate towards proximal circumferential groove 34. As sleeve lock 2 translates, anti-rotation tab 11 slides in nail body 1 sleeve lock anti-rotation groove 36 thus preventing relative rotation between sleeve lock 2 and the nail body 1. Since end cap 8 slots 20/50 were aligned with nail body 1 sleeve lock anti-rotation slot 36, sleeve lock anti-rotation tab 11 is aligned with end cap 8 slots 20/50. As sleeve lock 2 continues to translate towards end cap 8, sleeve lock anti-rotation tab 11 enters/mates with end cap slots 20/50 and snap ring 7 enters nail body proximal circumferential groove 34 "detenting" sleeve lock 2 into position. With sleeve lock 2 in this position, nail body anti-rotation slot 36, sleeve lock tab 11 and end cap slots 20/50 are in a mated condition (FIG. 6). This prevents any relative rotation of nail body 1, sleeve lock 2 and end cap 8 during handling or attachment of the installation instrumentation. The nail assembly is supplied for surgery in this condition. This preassembled condition saves surgical time over current intramedullary nail systems that require an end cap and setscrew to be added during surgery.

Figure 5:
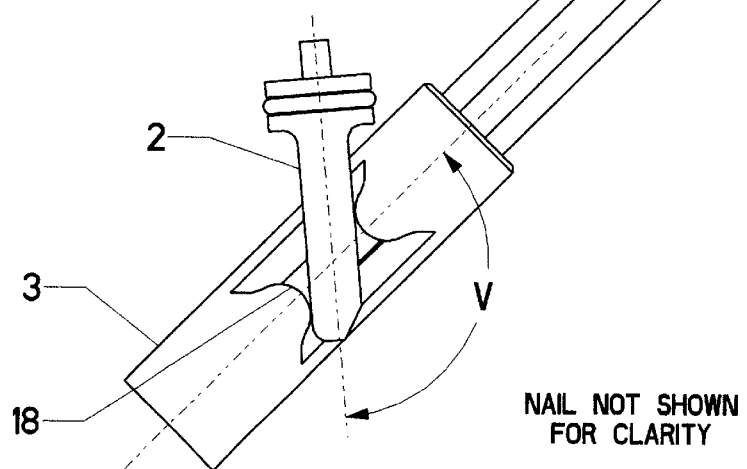
FIG. 5, is an enlarged view of the proximal portion of the Intramedullary Nail System of FIG. 3.
Figure 11:
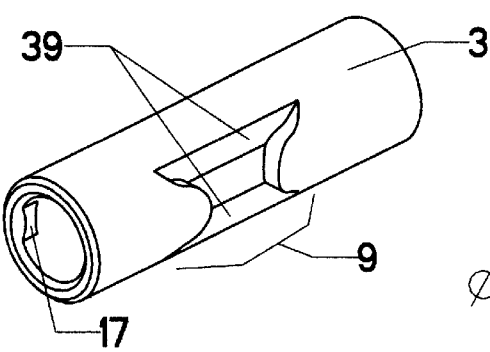
FIG. 11, is an isometric view of the Slotted Sleeve.
Figure 12:
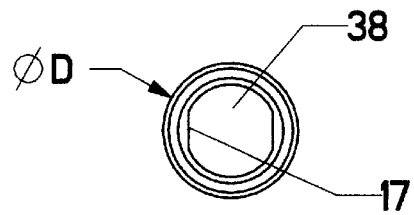
FIG. 12, is a top view of FIG. 11.
Figure 13:
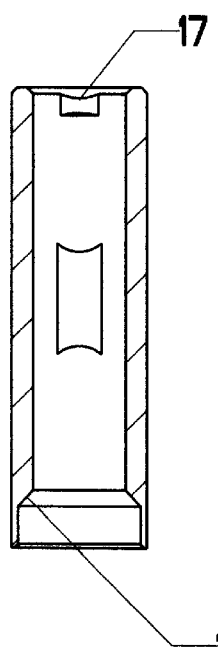
FIG. 13, is a section view of FIG. 11.
Figure 14:
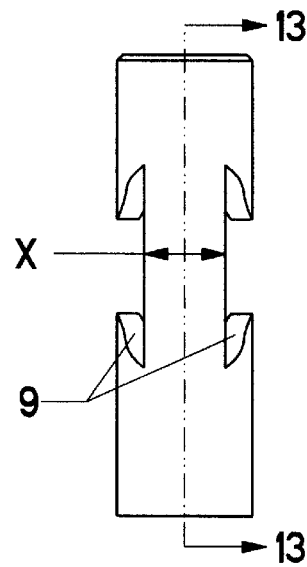
FIG. 14, is a front view of FIG. 11.
Figure 15:
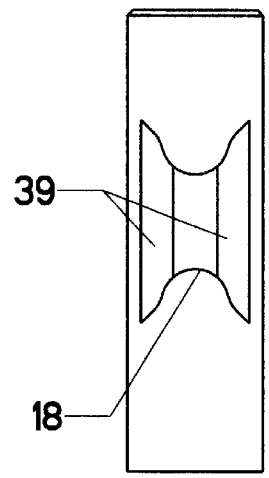
FIG. 15, is a side view of FIG. 11.

Sleeve 3 (FIG. 1) is utilized to secure lag screw assembly 4 into nail body bore 33 after implantation of the lag assembly 4 and nail body 1 in the femur. The outside diameter D (FIG. 12) is sized for a sliding fit in bore 33. The sleeve 3 has a circular bore 38 and a small length of bore having oppositely disposed flats 17 at the leading end (FIGS. 11,12,13). These are sized for a sliding fit with the body 30 and flats 29 of lag screw assembly 4 thus allowing axial translation of lag screw assembly 4 but not allowing relative rotation. The sleeve 3 contains two locking slots 9 (FIGS. 11, 14), which continue through sleeve 3 wall thickness and are located opposite each other (180 degrees radially) on the sleeve 3 body. These slots 9 are comprised of two features in addition to the opening into the sleeve bore 38. They are the flats 39 and the anti-translation bosses 18. The distance X (FIG. 14) between flats 39 of each slot 9 is sized for a sliding fit in the space Y between locking tabs 10 of sleeve lock 2 (FIG. 9). The anti-rotation bosses 18 are configured and spaced in such a way as to provide a sliding fit when sleeve 3 and sleeve lock 2 are mated at a relative angle V as shown in FIG. 5. The locking slots 9 configuration still functions when angle V is varied over a small range. A counterbore 19 is provided in the end of sleeve 3 opposite that of the flats 17 and has the configuration as shown in FIG. 13. It is sized and configured for mating with compression screw 6 as shown in FIG. 2.

The nail assembly consisting of nail body 1, sleeve lock 2, snap ring 7 and end cap 8 is inserted in an antegrade fashion into the femur. Prior to insertion, an instrument is attached to the proximal end of the nail assembly. The instrument (not shown) utilizes the threaded bore 16 of end cap 8 for attachment and incorporates a protruding feature which mates simultaneously with slot 26 of nail body 1 and slot 50 of end cap 8. This provides angular alignment between the instrument and the nail body 2 and provides anti-rotation of end cap 8 within nail body 1 during attachment/torqueing of the instrument into threaded bore 16 of end cap 8. The nail assembly is inserted into the femur and the lag screw assembly 4 is then inserted through nail body bore 33. Instrumentation assures proper insertion depth of lag screw assembly 4 and alignment of the plane of lag screw flats 29 parallel to the nail body proximal bore 32 longitudinal axis. After the lag screw 4 is implanted in its proper position within the femur, its trailing end protrudes partially or fully through nail body 1 bore 33. The leading end of sleeve 3 containing flats 17 is inserted into bore 33 and the bore 38 of sleeve 3 aligned, with the aid of instrumentation (not shown) with the similarly shaped lag screw body 30. The sleeve 3 is inserted further into bore 33 thus mating with lag screw 4. Since, as described previously, sleeve flats 17 interact with lag screw flats 29 preventing relative rotation between lag screw 4 and sleeve 3 and the plane of lag screw flats 29 are already aligned parallel to nail proximal bore 32 longitudinal axis the plane of the sleeve flats 39 are now also aligned parallel with the nail proximal bore 32 longitudinal axis. Instrumentation (not shown) has also located the centerline of sleeve 3 slots 9 coincident to the longitudinal axis of nail body proximal bore 32 and therefore also coincident with sleeve locking tab 10 longitudinal axis. The sleeve lock 2, snap ring 7, sleeve 3 and lag screw 4 are now in the relative positions as shown in FIG. 4.

The sleeve lock 2 and snap ring 7 are now translated by instrumentation (not shown), as previously described, such that snap ring 7 moves from nail body proximal circumferential groove 34 to nail body distal circumferential groove 35 and sleeve locking tabs 10 mate into sleeve slots 9 as shown in FIG. 5. With sleeve 3, sleeve lock 2, snap ring 7 and lag screw 4 assembled as shown in FIG. 5 within nail body 1, sleeve 3 is fixed in rotation by interaction of locking tabs 10 and sleeve flats 39 and in translation by interaction of locking tabs 10 with sleeve anti-translation bosses 18. Since sleeve 3 is now fixed in rotation, lag screw 4 is also fixed in rotation by the interaction of sleeve flats 17 and lag screw flats 29 but not fixed in translation. The end cap 8 remains in position and is utilized to prevent bony ingrowth into nail body internal threads 37, which are used for removal instrument interface, if nail assembly removal is required in the future.

With sleeve 3 and lag screw 4 fixed in rotation, tangs 12 of lag screw 4 can be deployed as described in U.S. Pat. No. 6,183,474 B1. After tang 12 deployment, compression screw 6 is inserted through bore 38 of sleeve 3 mating its threaded end with internal threads within lag screw 4 and its head with sleeve counterbore 19. As compression screw 6 is tightened, its head contacts sleeve counterbore 19, and since sleeve 3 is fixed in translation by locking tabs 10, lag screw 4 is drawn toward nail body 1 thereby compressing the fracture.

One or two cortical screws 5 can now be used to fix nail body 1 both in translation and rotation within the intramedullary canal. The cortical screws 5 are placed through the lateral femoral cortex and through clearance holes 25 in the nail body 1, then through the medial femoral cortex (FIG. 2).

The nail assembly can be removed by removing cortical screws 5, compression screw 6, retracting tangs 12, as described in detail in U.S. Pat. No. 6,1834,74 B1, removing end cap 8, releasing sleeve 2 by translating sleeve lock 2 and snap ring 7 to nail body proximal circumferential groove 34, removing sleeve 2 and lag screw 4 and utilizing nail body internal threads 37 to interface a nail body 1 removal instrument (not described) and pull the nail body from the intramedullary canal.

In an alternate kit embodiment (FIG. 25), sleeve lock 2, end cap 8 and snap ring 7 are replaced by sleeve lock assembly 42 (FIG. 33). The alternate configuration of sleeve lock 42 results in the nail body 1 not requiring sleeve lock anti-rotation groove 36, proximal and distal circumferential grooves 34 and 35. In this embodiment, no implant components are assembled into the nail body 1 prior to its insertion into the femur.

Figure 29:
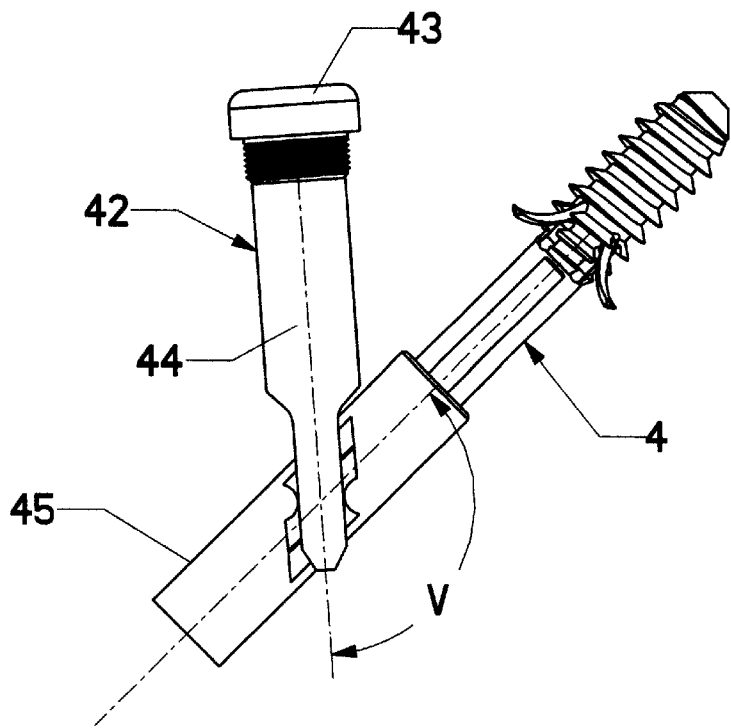
FIG. 29, is an enlarged proximal view of the alternate embodiment Intramedullary Nail System of FIG. 25.
Figure 30:
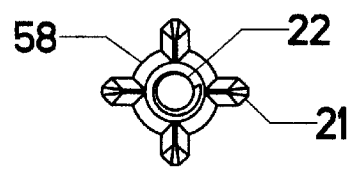
FIG. 30, is an enlargement of the Tang Assembly in FIG. 32.

End cap assembly 42 consists of two parts, end cap 43 and bifurcated sleeve lock 44 (FIG. 33). The end cap 43 contains drive interface 46 (FIG. 34) which provides a means to drive the end cap with an instrument and an external thread 49 (FIG. 35) sized to interface with nail body internal thread 37 (FIG. 20). The bifurcated sleeve lock 44 incorporates a cylindrical peened interface 48 (FIG. 36) which protrudes through a clearance hole in end cap 43 and into drive interface 46 where it is peened over in such a way as to retain end cap 43 to bifurcated sleeve lock 44 but allow relative rotation of the two parts. Locking tabs 47 have a semicircular cross section with a radius equal to that of the body of the bifurcated sleeve lock 44 sized to provide a sliding fit in proximal bore 32 of nail body 1 and a width sized to provide a sliding fit between sleeve anti-rotation bosses 18 when the parts are assembled at angle V as shown in FIG. 29. Angle V can vary over a range and the fit will still be maintained. Distance Z (FIG. 35) is such as to provide a sliding fit over dimension X of sleeve 3.

Unlike the preferred embodiment, sleeve lock assembly 42 is not pre-assembled into nail body but is instead installed as a last step in the procedure. The nail body 1 is inserted into the intramedullary canal of the femur, the lag screw 4, sleeve 3, compression screw 6 are installed as well as the cortical screws 5. The nail body 1 insertion instrument (not shown) is then removed from the proximal end of nail body 1 and the locking tab 47 (FIG. 33) end of sleeve lock assembly 42 is inserted into the proximal bore 32 of the nail body 1. It must be manipulated to align with sleeve 3 slots 9. Note that this manipulation could be eased through the addition of a keying feature between the bifurcated sleeve lock 44 and the nail proximal bore 32. Once aligned, locking tabs 47 will enter and mate with sleeve slots 9 allowing the sleeve lock assembly to translate far enough for threads 49 of end cap 43 to mate with nail body internal threads 37. Since the peened interface between end cap 43 and bifurcated sleeve lock 44 allow relative rotation, drive interface 46 can be used to fully engage threads 49 and 37. The sleeve is now fixed in rotation and translation as previously described. The nail assembly can be removed by reversing the assembly order.

Figure 25:
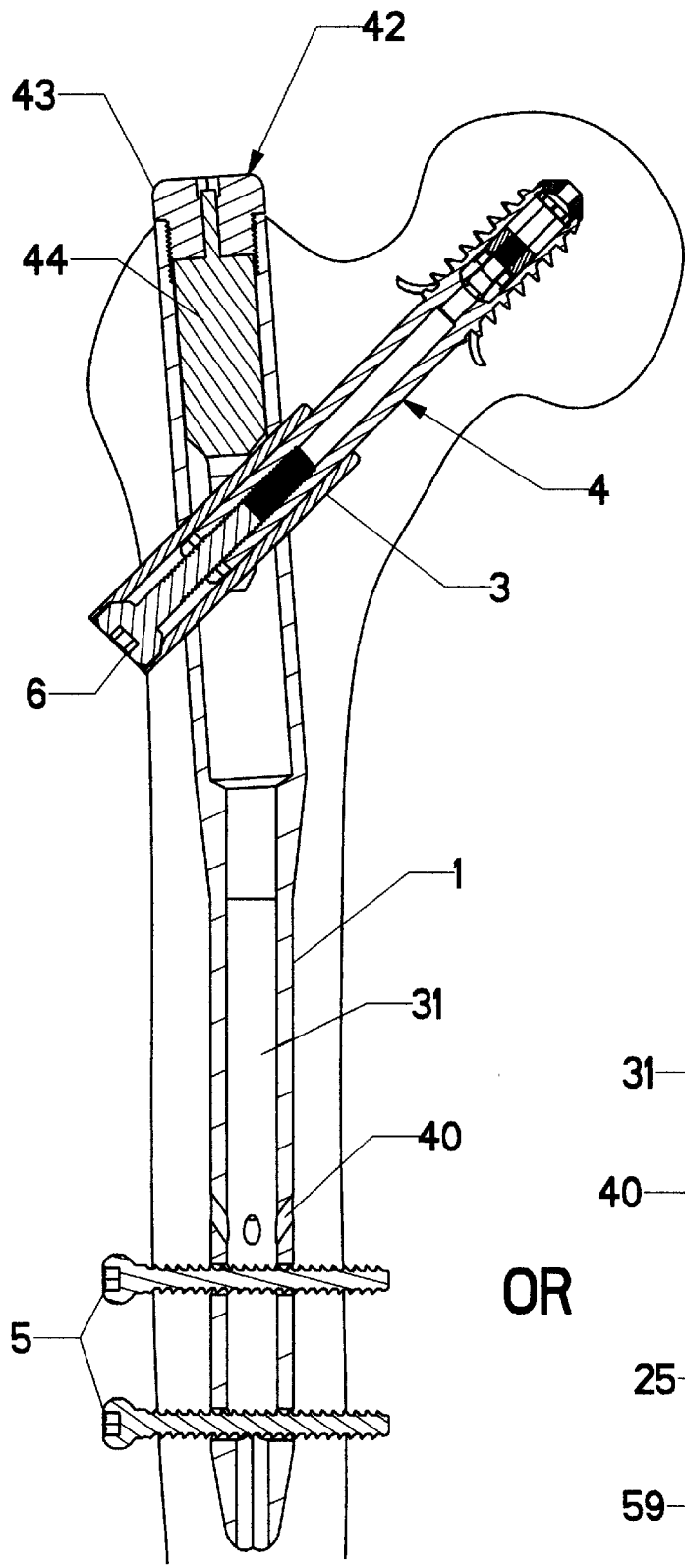
FIG. 25, is a view, partially in longitudinal cross section, of the alternate embodiment Intramedullary Nail System placed in the intramedullary canal of a fractured bone using cortical screws as a method of fixation.
Figure 25A:
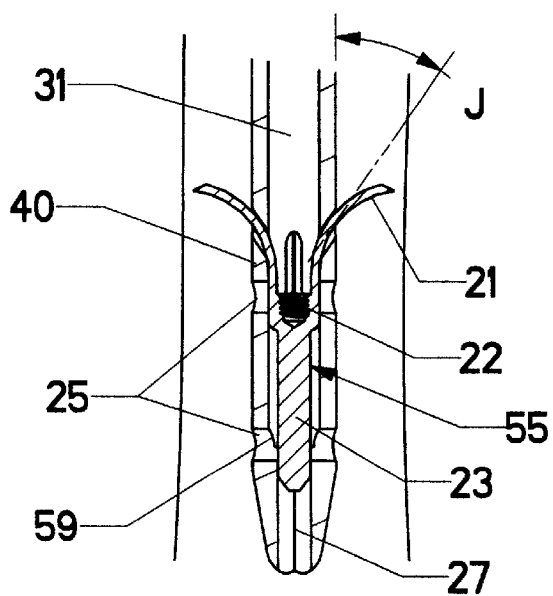
FIG. 25A, is an enlarged view of the distal portion, of the alternate embodiment Intramedullary Nail System in FIG. 25 using the talon as a method of fixation.

This alternate embodiment also allows another method for rotational and translational locking of the nail assembly distally in the intramedullary canal. Instead of cortical screws 5, use of a distal tang 55 would be optional (FIG. 25A). Note that this distal tang 55 would have to be inserted prior to the installation of the sleeve 3, lag screw assembly 4 and compression screw 6.

Figure 31:
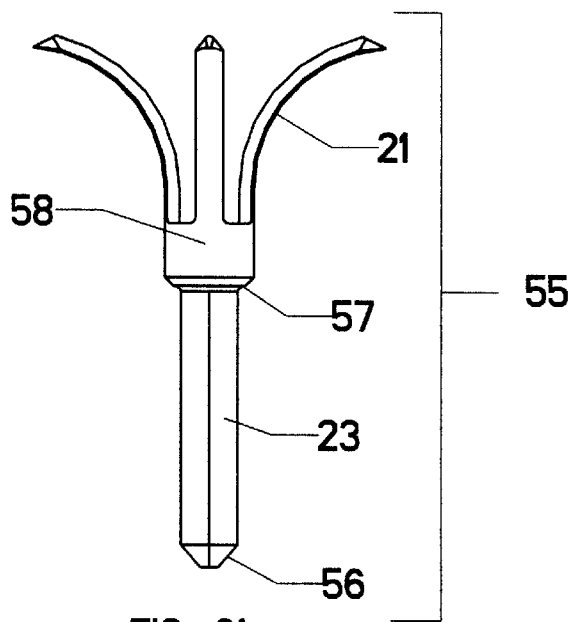
FIG. 31, is a front view of the deployed Tang Assembly.

In this embodiment, the distal end of nail body 1 would incorporate an end hole of square cross section 27 (FIG. 25A) and four tang exit holes 40 in addition to the cortical screw holes 25. Distal bore 31 is sized to permit a sliding fit with the tang body 58 (FIG. 31). Four tang exit holes 40 (FIG. 28) are located on a 90 degree radial spacing penetrating from the distal outside diameter E into the distal bore 31, on axes which form an angle J (FIG. 25A). The clearance holes 25 pass through the distal outside surface and wall into the distal bore 31 and continue on the same axis through the opposite wall and outer diameter. Their diameter is such as to allow passage of the threaded portion of the cortical screw 5 (FIG. 1). A frustro-conical feature 59 (FIG. 25A) provides a transition between the circular bore 31 and the square bore 27. The square bore 27 serves three purposes. It provides clearance through the leading end of the nail body for passage of a guide pin, used during fracture alignment and installation of the of the nail body into the intramedullary canal, it provides a sliding fit for the square forward protrusion 23 (FIG. 31) of tang 3, and it acts as a "vent" hole for any organic material within the bore 31 which is being pushed ahead of the tang during tang installation. It must be noted that the forward most clearance holes 25 also intersect the frustro-conical feature 59 and will act as vents for organic material during tang insertion after the square protrusion 23 has engaged and filled square bore 27.

Figure 32:
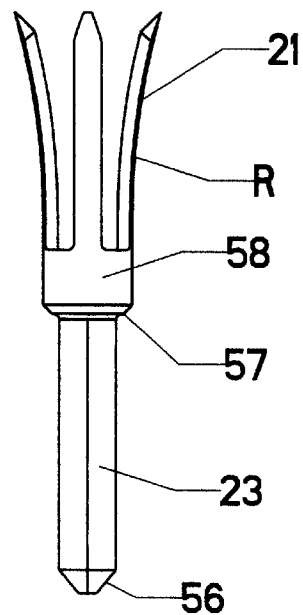
FIG. 32, is a front view of the stowed Tang Assembly.

The tang 55 has four equally sized and radially spaced legs which are preformed to radius R. The radius R (FIG. 32) on each leg 21 results in a dimension between the trailing ends of opposing legs which is greater than the outside diameter of tang body 58 and the bore diameter 31 of nail body 2. The tang body 58 is circular in cross section and sized for a sliding fit within nail body bore 31 with a leading edge chamfer 57 which transitions into the leading protrusion 23 which has a square cross section and leading end taper 56. Tang body 58 contains an internally threaded bore 22 which is the instrument interface for the instrument 51 used to insert and deploy the tang. It must be noted that threaded bore 22 is not needed for tang retraction. FIG. 31 illustrates the deployed shape of tang 55 which is the shape it assumes after the legs 21 have been forced through the tang exit holes 40 of nail body 1.

Figure 26:
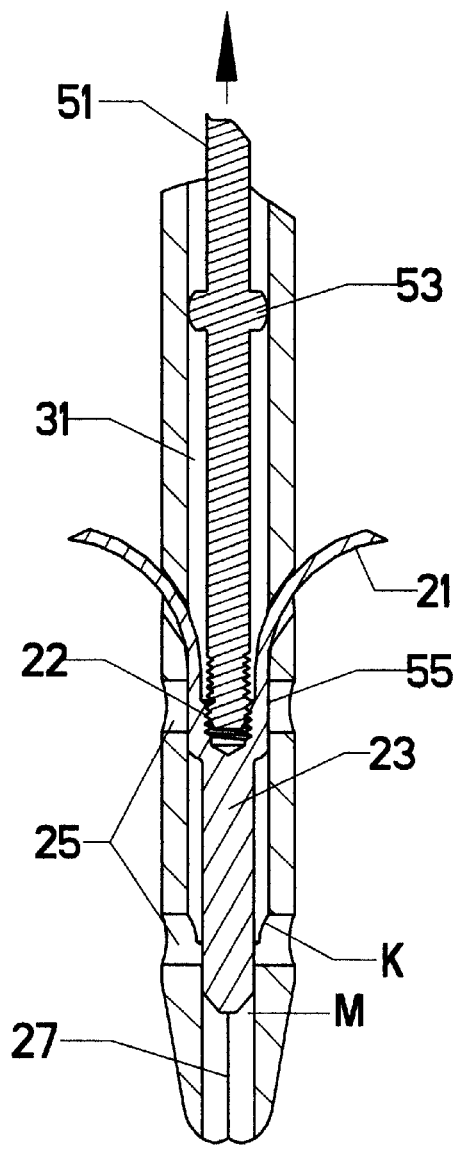
FIG. 26, is an enlarged view of the distal portion, of the alternate embodiment Intramedullary Nail System in FIG. 25 during Tang Assembly deployment.
Figure 27:
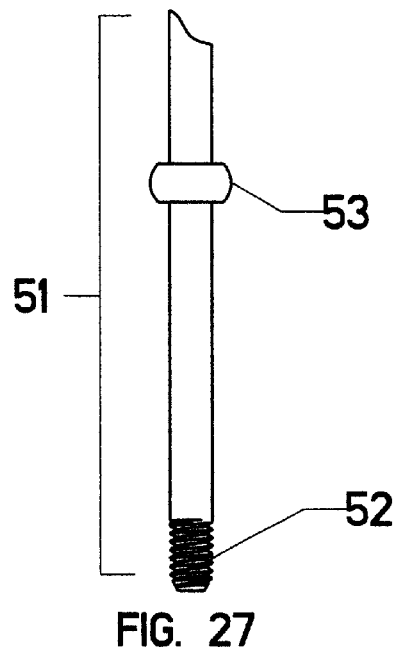
FIG. 27, is an enlarged, partial view of the Tang Actuator Assembly of FIG. 26.
Figure 28:
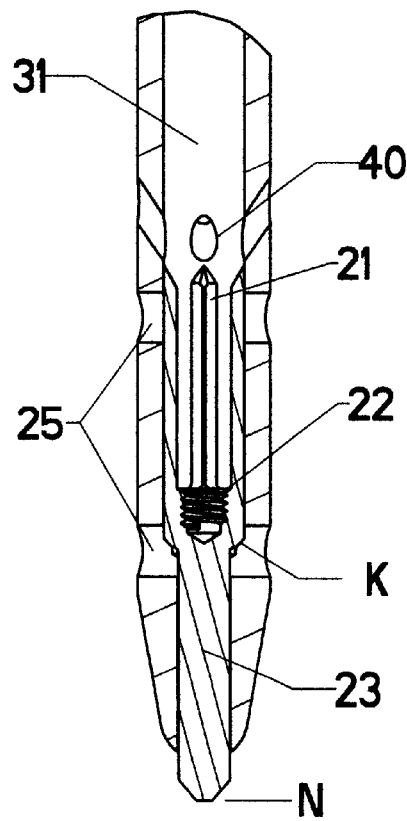
FIG. 28, is an enlarged view of the stowed Tang Assembly from FIG. 25A.

Insertion/deployment of the tang 55 occurs after insertion of the nail body into the intramedullary canal. The insertion/deployment instrument 51 (FIG. 27) has threads 52 that are mated with tang 55 threaded bore 22. The tang 55 is now inserted through nail body bore 32 and into nail body bore 31. The insertion/deployment instrument 51 has a self-centering bushing 53 to help orient the tang 55 for proper insertion. Since the distance between opposing tang legs 21 is greater than the bore diameter 31 due to radius R, the interference with bore 31 forces the legs 21 inward in an elastic manner and insertion continues with some resistance. As the tang travels down bore 31, any organic material which has accumulated in bore 31 is pushed ahead and forced out through square bore 27 of nail body 1 and through cortical screw clearance holes 25. Further insertion causes the tang 55 leading square taper 56 to contact the square bore 27 of the nail body 1. Since both cross sections are square, no engagement will occur until they are radially aligned which may or may not occur without some slight rotation of the tang 55 using the insertion/deployment instrument 51 (FIG. 27). After alignment occurs and by virtue of this alignment, the tang leading protrusion 23 will slide freely in square bore 27 and the tang legs 21 and the nail body 1 tang exit holes 40 will now be aligned. The tang 55 continues past tang exit holes 40 and is fully inserted when the tang body leading edge chamfer 57 makes contact with the nail body frustroconical feature 59 at point K (FIG. 28). In this position, the leading end of tang 55 protrudes through the end of nail body 1 to point N and the trailing end of the tang legs 21 are just past tang exit holes 40. The tang is now in position to be deployed. To deploy the tang, an axial force is exerted by the insertion/deployment instrument 51 in the opposite direction as for insertion. This causes the tang 55 to translate back up bore 31 and the sharp ends of tang legs 21 to encounter tang exit holes 40. Since the tang legs 21 were elastically compressed inward by bore 31 they will now spring outward forcing the sharp end of tang legs 21 into tang exit holes 40. Further translation of the tang 55 forces the tang legs through the tang exit holes 40. Due to the diameter and angle of the tang exit holes 40, the tang legs 21 are formed in such a manner as to emerge almost perpendicular to the femoral cortex (FIG. 25A). Continued translation of the tang 55 causes the tang legs 21 to penetrate the femoral cortex. During this time, tang leading square protrusion 23 is still engaged by the nail body square bore 27 thus preventing rotation of tang 55 in bore 31 during deployment and preventing unwanted twisting of the tang legs 21. The tang 55 can be deployed fully or partially and is self-locking in any position due to the almost perpendicular entry angle into the femoral cortex. After deployment, the insertion/deployment instrument 51 is unthreaded from tang threaded bore 25 and removed. The nail body 1 is now fixed axially and rotationally in the intramedullary canal. FIG. 26 shows the tang 55 in the fully deployed position having translated a distance from point N (FIG. 28) to point M (FIG. 26). The tang 55 is fully retractable. It is retracted by applying a force on the tang 55 with instrumentation in the opposite direction as deployment until the tang 55 comes to rest at points K and N as shown in FIG. 28.

Note that at the surgeon's discretion, distal fixation of the nail body 1 can still be accomplished without use of tang 55. This is accomplished by using the cortical screws 5 (FIG. 1) as described in the preferred embodiment. The cortical screws 5 are placed through the lateral femoral cortex and through clearance holes 25 in the nail body 1, and through the medial femoral cortex (FIG. 25). The cortical screws are not used in conjunction with distal tang fixation and cannot be passed through clearance holes 25 if there is a tang 55 inserted into nail body 1.

It should be noted that this description is directed at only one possible alternate embodiment and that many others are possible ending with the same results without departing from the spirit and scope of the invention. As examples, tang 55 could have any number of legs 21, square protrusion 23 could take on any keyed polygon shape, sleeve lock 2 could be made with 1 leg 10 and the lag screw may or may not have tangs.

We claim:

1. An intramedullary nail for insertion in the intramedullary canal of a long bone comprising a nail body having a leading end and a trailing end, said trailing end having an axial bore and an intersecting transverse clearance bore, said body having at least one portal therethrough near said leading end adapted to receive at least one anchor extending through said leading end to secure said nail body in the intramedullary canal, a lag screw assembly adapted to slidably extend through said transverse clearance bore, said lag screw assembly having a body with a leading end and a trailing end, said leading end having a tang for purchase in bone, a sleeve lock is movably disposed at a first position in said axial bore between said trailing end and said transverse clearance bore, said sleeve lock having at least one locking tab extending toward said transverse clearance bore in said axial bore.

2. An intramedullary nail as claimed in claim 1 wherein said at least one portal is a clearance hole and said at least one anchor is a cortical screw.

3. An intramedullary nail as claimed in claim 1 wherein said axial bore extends into said leading end, said at least one portal is an exit hole from said axial bore through said nail body, said at least one anchor includes a tang body disposed in said axial bore in said leading end, said tang body having at least one tang adapted to extend through said exit hole to secure said nail body.

4. An intramedullary nail as claimed in claim 3 wherein said leading end includes at least one clearance hole adapted to receive a cortical screw.

5. An intramedullary nail as claimed in claim 1 wherein said lag screw assembly leading end having external threads for purchase in bone.

6. An intramedullary nail as claimed in claim 5 wherein said lag screw body has an axial bore and said external threads include at least one exit hole from said bore, a tang body disposed in said bore, said tang body having at least one tang adapted to extend through said at least one exit hole to increase purchase of said lag screw assembly.

7. An intramedullary nail as claimed in claim 5 wherein said axial bore extends into said leading end, said at least one portal is an exit hole from said axial bore through said nail body, said at least one anchor includes a tang body disposed in said axial bore in said leading end, said tang body having at least one tang adapted to extend through said at least one exit hole to secure said nail body.

8. An intramedullary nail for insertion in the intramedullary canal of a long bone comprising a nail body having a leading end and a trailing end, said trailing end having an axial bore and an intersecting transverse clearance bore, said body having at least one portal therethrough near said leading end adapted to receive at least one anchor extending through said leading end to secure said nail body in the intramedullary canal wherein a lag screw assembly is adapted to slidably extend through said transverse clearance bore, said lag screw assembly having a body with a leading end and a trailing end, said leading end having external threads for purchase in bone wherein a sleeve lock is movably disposed at a first position in said axial bore between said trailing end and said transverse clearance bore, said sleeve lock having at least one locking tab extending toward said transverse clearance bore in said axial bore.

9. An intramedullary nail as claimed in claim 8 wherein a sleeve having a tubular sidewall is adapted to slidably extend through said transverse clearance bore around said lag screw assembly, said side wall of said sleeve having at least one slot therein, and said at least one locking tab engaging said at least one slot when said sleeve lock is moved to a second position in said axial bore.

10. An intramedullary nail as claimed in claim 9 wherein said trailing end of said lag screw assembly and said sleeve are approximately co-terminus, said co-terminus ends are adapted for longitudinal translation relative to each other to transmit compressive force between said nail body and said leading end of said lag screw assembly.

11. An intramedullary nail as claimed in claim 10 wherein said lag screw body has an axial bore and said external threads include at least one exit hole from said bore, a tang body disposed in said bore having at least one tang adapted to extend through said at least one exit hole to increase purchase in a bone.

12. An intramedullary nail as claimed in claim 9 wherein said trailing end of said lag screw has a shaped exterior surface, said shaped exterior surface preventing relative rotation of said lag screw and said sleeve.

13. An intramedullary nail system kit for applying compressive force across a fracture, said kit comprising an intramedullary nail having a leading end, a trailing end, an axial bore, a transverse clearance bore in said trailing end intersecting said axial bore, and a plurality of portals through said leading end, a plurality of anchors adapted to extend through said portals, a lag screw with external screw threads on one end and internal screw threads on the other end, a sleeve having a bore with an internal diameter larger than said other end of said lag screw and an external diameter to slidably extend through said transverse clearance bore, said sleeve having at least one transverse slot exposing said bore, a sleeve lock sized to slide in said axial bore at said trailing end, said sleeve lock having at least one locking tab disposed in said axial bore extending toward said transverse clearance bore, and a compression screw with complimentary threads for the internal threads of said lag screw, said compression screw having a shoulder for engaging said sleeve, said kit including a subassembly with said sleeve lock disposed at a first fixed position in said trailing end of said axial bore of said intramedullary nail whereby said kit is assembled by inserting said lag screw through said transverse bore, inserting said sleeve over said lag screw through said transverse bore and aligning said at least one slot with said axial bore, sliding said sleeve lock of said subassembly to a second fixed position in said axial bore engaging said at least one locking tab with said at least one slot preventing longitudinal and rotational movement between said sleeve and said nail, turning said compression screw in said internal screw threads of said lag screw so that said shoulder engages said sleeve providing longitudinal translation between said sleeve and said lag screw producing compressive force between said nail and said lag screw and inserting said anchors through said portals.

14. An intramedullary nail system kit as claimed in claim 13 wherein said kit includes another subassembly with a cannulated nail, said cannulated nail having a plurality of portals in said leading end, a tang body disposed in said leading end of said cannulated nail having a plurality of tangs adapted to extend through said plurality of portals.

15. An intramedullary nail system kit as claimed in claim 14 wherein said kit includes a third subassembly with said lag screw having a bore from said leading end to said trailing end, said leading end of said lag screw having a plurality of exit holes from said bore through said external screw threads, a tang body disposed in said leading end of said bore having a plurality of tangs adapted to extend through said exit holes whereby said kit is assembled by manipulating said tang body to extend said tangs through said exit holes.

16. An intramedullary nail system comprising an intramedullary nail for implantation in a long bone, said intramedullary nail having a leading end, a trailing end, and an axial bore therethrough, a transverse clearance bore intersects said axial bore in said trailing end, portals through said leading end from said axial bore, a tang body movably disposed in said leading end having tangs extending through said portals, a sleeve slidably disposed in said transverse clearance bore, said sleeve having a tubular side wall and a bore, a slot in said sidewall exposing said bore, said bore of said sleeve having an internal surface, a portion of said internal surface formed in a flat shape, a lag screw slidably disposed in said sleeve, said lag screw having a body and a leading end, external screw threads on said leading end, internal screw threads in said body, said body having an external surface formed in a flat shape, said flat shape of said internal surface of said sleeve and said flat surface of said external surface of said lag screw engaged to prevent relative rotation between said sleeve and said lag screw, said slot in said sleeve disposed in said axial bore of said nail, a sleeve lock slidably fixed in said axial bore between said trailing end and said clearance bore, said sleeve lock having a depending locking tab extending in said axial bore toward said sleeve, said locking tab engaging said slot preventing relative rotation and longitudinal translation of said sleeve and said nail, an end cap in said trailing end of said axial bore closing said bore and engaging said sleeve lock, and a compression screw engaging said internal threads in said lag screw body, said compression screw having a shoulder engaging said sleeve providing relative longitudinal translation between said lag screw and said sleeve.

* * * * *